United States Patent
Hanssen

(10) Patent No.: US 6,167,885 B1
(45) Date of Patent: Jan. 2, 2001

(54) METHOD AND APPARATUS FOR CONTROLLING THE BODY TEMPERATURE OF A PATIENT

(75) Inventor: Carl-Otto Hanssen, Kullavik (SE)

(73) Assignee: Molnlycke Health Care AB, Gothenburg (SE)

( * ) Notice: Under 35 U.S.C. 154(b), the term of this patent shall be extended for 0 days.

(21) Appl. No.: 09/242,325

(22) PCT Filed: Aug. 12, 1997

(86) PCT No.: PCT/SE97/01342

§ 371 Date: Mar. 11, 1999

§ 102(e) Date: Mar. 11, 1999

(87) PCT Pub. No.: WO98/06361

PCT Pub. Date: Feb. 19, 1998

(30) Foreign Application Priority Data

Aug. 14, 1996 (SE) .................................................. 9602978

(51) Int. Cl.[7] .................................................. A61B 19/00
(52) U.S. Cl. .................................................. 128/849; 128/853
(58) Field of Search .................................... 128/847, 849–856

(56) References Cited

U.S. PATENT DOCUMENTS

| | | | |
|---|---|---|---|
| 3,403,677 | * 10/1968 | Struve | 128/847 |
| 3,763,857 | * 10/1973 | Schrading | 128/853 |
| 4,367,728 | * 1/1983 | Mutke | 128/853 |
| 4,476,860 | * 10/1984 | Collins | 128/853 |
| 5,044,364 | 9/1991 | Crowther . | |
| 5,405,370 | 4/1995 | Irani . | |
| 5,443,488 | 8/1995 | Namenye et al. . | |
| 5,514,169 | 5/1996 | Dickerhoff et al. . | |
| 5,522,871 | 6/1996 | Sternlicht . | |
| 5,588,968 | 12/1996 | Sternlicht . | |

FOREIGN PATENT DOCUMENTS

WO 94/01051    1/1994   (WO) .

* cited by examiner

Primary Examiner—Michael A. Brown
(74) Attorney, Agent, or Firm—Young & Thompson

(57) ABSTRACT

A method for controlling the condition of a patient lying on an operating table during the course fo a surgical operation. At least one air-impervious surgical drape that includes an operation opening is laid over the patient, so that the surgical drape, or drapes, will hang down from the operating table along its long sides and short sides and therewith form an upwardly and laterally closed space whose roof and walls are formed by the surgical drape, or drapes. Conditioned air is delivered to the closed space by an air-conditioning unit, which includes an air outlet opening through which air can leave the closed space.

14 Claims, 2 Drawing Sheets

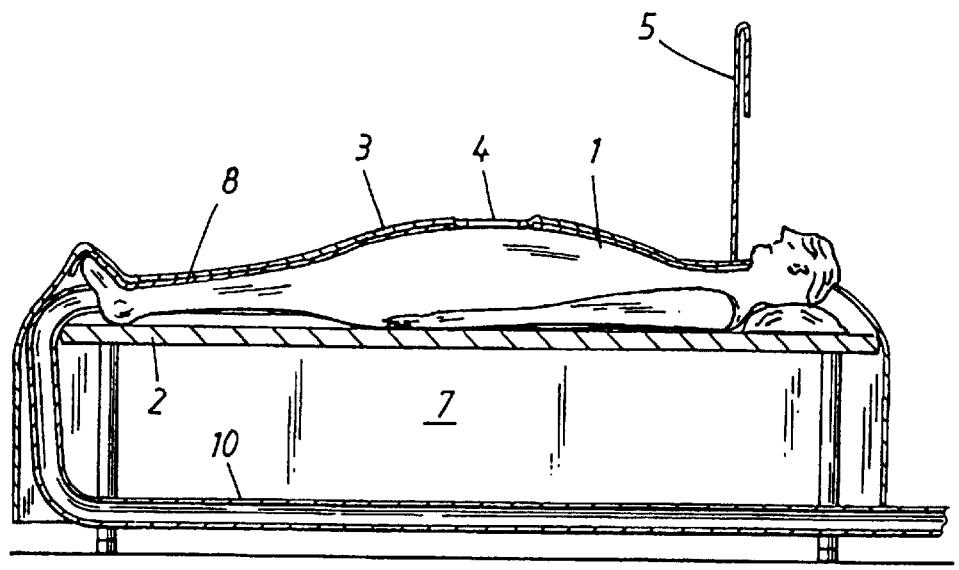
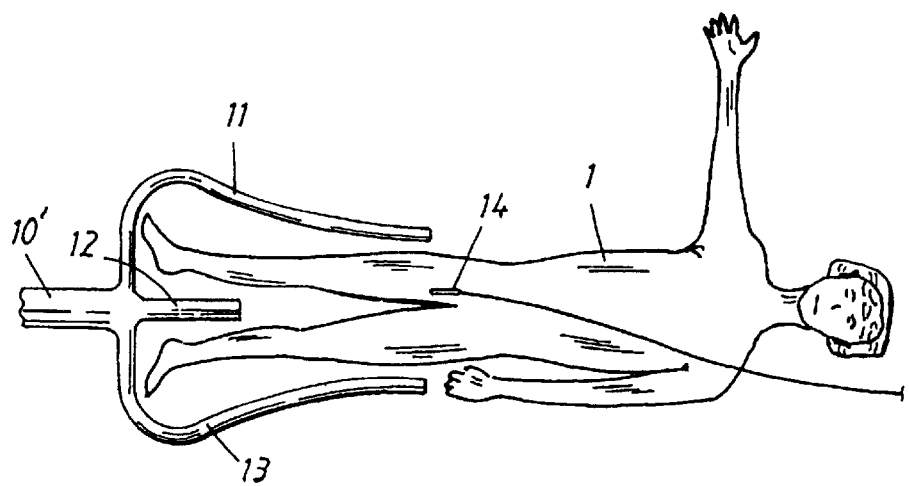

METHOD AND APPARATUS FOR CONTROLLING THE BODY TEMPERATURE OF A PATIENT

CROSS REFERENCE TO RELATED APPLICATION

This is the 35 USC 371 National Stage of International application PCT/SE97/01342 filed on Aug. 12, 1997, which designated the United States of America.

The present invention relates to a method of providing means for controlling the condition of a patient lying on a operating table during the course of surgery and also to means provided by the method.

BACKGROUND OF THE INVENTION

One problem with surgical operations that take a long time to perform resides in the risk of hypothermia, i.e. the risk of the patient's body temperature falling beneath 36° C. At this temperature the function of the central nervous system and the endocrine system is disturbed, giving rise to undesirable physiological changes. Hypothermia can develop suddenly as a result of several different factors, for instance cold operating theatres, anaesthesia with dampening of the central nervous system, lowered metabolism and blood vessel dilation, intravenous liquids, unprotected patients who lie motionless, and large stomach-thorax openings. In order to reduce the risk of hypothermia in the case of surgical operations of long duration it is known to place heating blankets or the like on the patient. See, for instance, EP-B1-0 311 336, EP-A2-0 511 743 and U.S. Pat. No. 5,350,417. These prior publications teach so-called warm-air blankets or covers which consist of two sheets between which warm air is delivered under pressure. The bottom sheet of the warm-air sheets is perforated to provide a down-flow of warm air. The construction of these known warm-ark blankets, or covers, is relatively complicated and the blankets demand a relatively high price. Furthermore, each type of operation required a warm-air blanket that is designed especially for that particular operation which is reflected in the cost of production and also in user storage costs.

It is sometimes desirable to induce hypothermia in conjunction with certain types of surgery, for instance heart and brain surgery.

SUMMARY OF THE INVENTION

The object of the present invention is to provide a method of providing means for controlling the condition of a patient lying on an operating table during the course of surgery, said method enabling said means to be constructed in a very simple fashion and to be used for several different types of surgical operations. The method also provides a satisfactory solution to the problem of carrying away unsterile air from the patient in a hygienic fashion. Another object of the present invention is to reduce the costs of controlling the condition of a patient in comparison with known means for achieving the same end.

The object is achieved in accordance with the invention by means of a method of providing means for controlling the condition of a patient lying on a operating table during the course of a surgical operation, said method being characterized by placing over the patient at least one air-impervious surgical drape that includes an operation opening, such that the drape or drapes hangs/hand down from the operating table along the long sides and short sides thereof so as tho form a space that is closed at its top and sides with the roof and walls of said space formed by the surgical drape or drapes; and by delivering conditioned air to the space with the aid of an air-conditioning unit, wherein an air outlet opening is provided to permit air to flow out from the closed space. This method enables the closed space to be provided with the use of air-impervious surgical drapes that are already available commercially, therewith enabling the provision of means that can be implemented in the performance of different types of surgical operations without needing to modify said means. Because the inventive method enables the use of surgical drapes that are already available commercially, the invention provides a highly cost-effective method fo controlling the condition of patients. The method can also be applied in a simple and uncomplicated manner and involves only a few further steps in addition to covering the patient in the usual way.

In one preferred embodiment of the invention, the air outflow opening is comprised of a gap between the bottom edges of the surgical drape and the floor of the operating theatre. A spacing sheet, which includes an operation opening corresponding to the operation opening in the surgical drape or in respective surgical drapes and which is somewhat stiffer than the drape material, is laid on the patient prior to laying the surgical drapes. The temperature of the patient is measured and the supply of or the temperature of the conditioned air is adjusted in dependence on the patient's temperature. The conditioned air is delivered to that part of the closed space which lies above the top of the operating table.

In one variant of the invention, the conditioned air is delivered through an inlet hose that opens into the upper part of the closed space defined by the surgical drapes.

The invention also relates to means for controlling the condition of a patient lying on an operating table during the course of a surgical operation. The means is characterized by at least one air-impervious surgical drape which has, or have, a shape and size such that when the drape or drapes has or have been placed over the patient in the manner intended parts of the drape or drapes will hang down from the operating table along its long and short sides without reaching the floor of the operating theatre and therewith form a space which is closed at the top and on the sides thereof, with the roof and walls of said space being formed by the surgical drape or drapes, and also by devices for delivering conditioned air to the closed space.

In one preferred embodiment of the invention, the means includes a spacing sheet which is intended to be laid over the patient prior to laying the surgical drapes and which is slightly stiffer than the drape material, and also includes a device for measuring the patient's temperature and a device for controlling the air supply means in dependence on the patient's measured temperature. Further, the amount of air delivered to said space or the temperature of said delivered air is controlled in dependence on the patient's measured temperature.

BRIEF DESCRIPTION OF THE DRAWINGS

The invention will now be described with reference to the accompanying drawings, in which

FIG. 3 is a sectioned view of the means shown in FIG. 1, and

FIG. 4 illustrates schematically a second embodiment of an inlet hose suitable for use in an inventive means.

DESCRIPTION OF THE PREFERRED EMBODIMENTS

Figure 1:
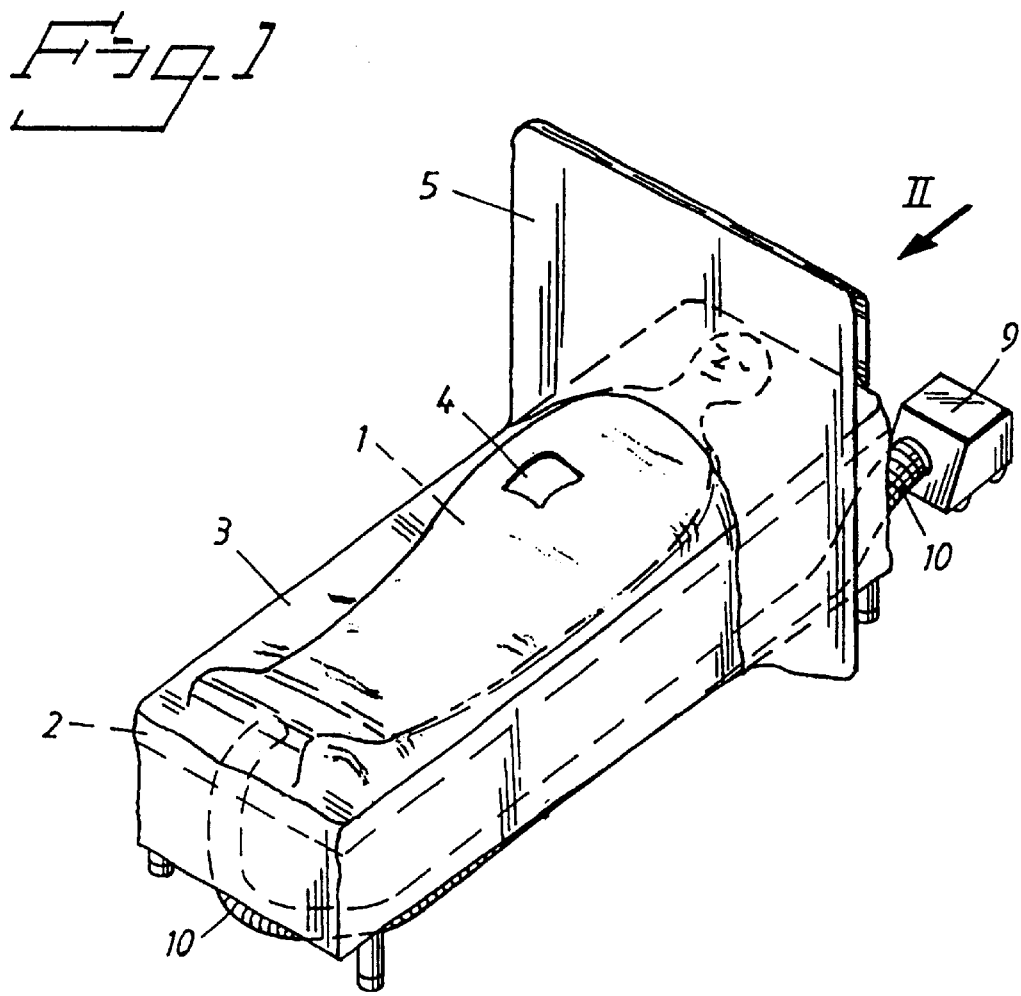
FIG. 1 is a schematic, perspective view of means for controlling the condition of a patient lying on an operating table during the course of a surgical operation, in accordance with a preferred embodiment of the invention.
Figure 2:
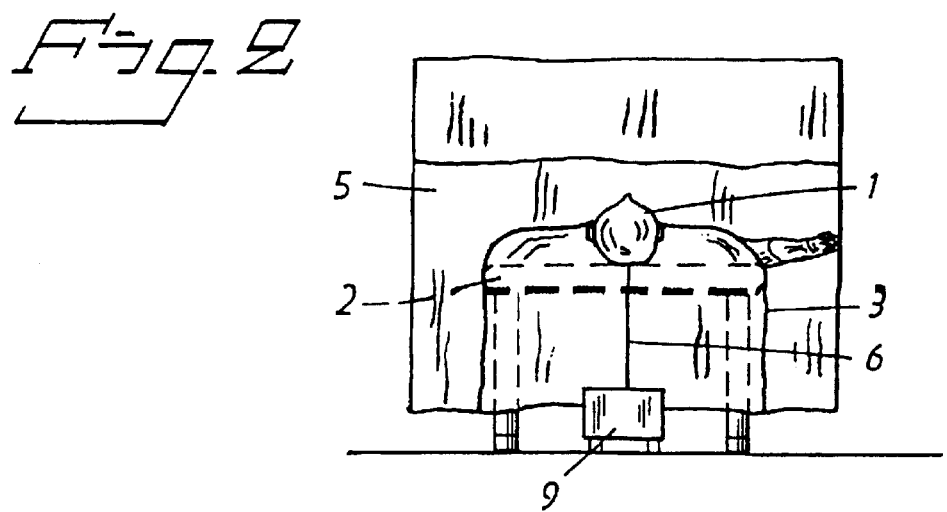
FIG. 2 is a view of the mean shown in FIG. 1, in the direction fo arrow II.

FIGS. 1, 2 and 3 are schematic illustrations of a patient 1 lying on an operating table 2. A surgical drape 3 that includes an operation opening 4 is shown placed over the patient. A further drape 5 is hung over an anaesthesia arch (not shown) at the table head. Further the surgical drape 3 is fastened to the patient's skin around the circumference of the operation opening 4, with the said of adhesive tape or in some other suitable manner. This will prevent air-carried or liquid-carried bacteria from being transmitted from the unsterile patient to the surgical area. Although the surgical drape 3 has been shown in the drawings as a single surgical drape, it will be understood that the drape may consist of several surgical sheets or drapes that have been fastened one to the other. Provided in the head-end part of the drape or sheet 3 is a longitudinally extending slit that extends to the head-end of the drape. This enables the drape to be placed around the patient's neck, whereafter the remaining part of the slit is closed and sealed with the aid of adhesive tape or clips. This method of draping a patient is essentially of conventional type.

The inventive method, however, requires the use of an air impervious surgical drape, for instance a drape marketed by Applicants under the trademark Kinidrape®.

When a patient is draped in the aforedescribed manner, which may, of course, also be achieved with the aid of several surgical drapes or surgical towels, there is formed an upwardly and laterally closed space 7 defined by a roof and side walls.

In the embodiment illustrated in FIGS. 1–3, a paper spacing sheet 8 which has essentially the same dimensions as that part of the operating table that extends from the anaesthetist's arch to the foot of the operating table is laid over the patient before the surgical drape 3 is placed in position. This spacing sheet is slightly stiffer than the drape material and prevents the surgical drape 3 from lying tightly against the patient's skin. Such a spacing sheet facilitates the circulation of air in the space between the drape 3 and the patient. Naturally, the spacing sheet 8 may be comprised of material other than paper, for instance a foamed plastic material. The spacing sheet 8 is, of course, provided with an opening corresponding to the operation opening 4 in the surgical drape 3.

Warm air, is delivered to the closed space with the aid of an appropriate warm-air unit 9, for instance the type of unit marketed by Gaymar Inc. under the trade name Theracare, and a flexible hose 10 which extends from the unit 9 beneath the bottom edges of the drape 3 and over the rear end of the table 2, so as to discharge between the legs of the patient lying on the table 2.

As warm air flows into the uppermost part of the space 7, the air present therein will be heated. Because the heated air rises, the upper part of the space 7 in which the patient is located will be the warmest part of the space. Naturally, cold air corresponding to the volume of warm air delivered to the space 7 must be removed from the space, this air leaking out through the gap between the floor of the operating theatre and the bottom edges of the drape 3. When the gap is sufficiently large, the resistance to the flow of cold air will be so small that the pressure in the space 7 will correspond essentially to ambient pressure. If desired, the drape may, of course, extend right down to the floor. In this latter case, an outlet hose is mounted in the space, which is now closed at its bottom, in the vicinity of the floor and connected to a suction unit which will extract the same amount of air as that delivered by the warm-air unit. It is, of course, conceivable to provide the drape 3 with outlet openings in the lower parts of its downwardly hanging portions, these openings either leading directly to the surroundings outside the space 7 or being connected to a suction unit.

As in the case of the warm-air covers known form the publications cited in the introduction, there is a risk that air circulating around the unsterile patient will contaminate the surroundings. However, the risk of air-carried contaminants reaching the surgical area is minimized through the invention partly because exhaust air form the space 7 is emitted in the vicinity of the theatre floor and partly because the rate at which air seeps from the space 7 is very low. The risk of such contamination can be fully eliminated by using an air extraction unit.

FIG. 4 illustrates another embodiment of an inlet hose 10' that can be used in an inventive means. The inlet hose 10' differs from the hose 10 shown in FIGS. 1 and 2 in that its end-part has the form of a tripod and includes three outlet pipes 11, 12 and 13. The outermost pipes 11 and 13 are longer than the centre pipe 12. An inlet construction of this configuration enables the air entering through the inlet hose to be distributed more effectively in the space between the drape 3 and the operating table and therewith obtain a uniform temperature in the space more quickly. The tripod-shaped end-part of the hose 10' may be made of a highly flexible material, and each pipe in the tripod is fastened to the operating table, e.g. with the aid of adhesive tape. Alternatively, the tripod-shaped end-part may be made of a stiffer material wherewith it suffices to fasten to the operating table that part of the hose 10' to which the tripod part is attached. The tripod part may alternatively consist of a separate element that can be connected to the remainder of the hose 10' with the aid of a suitable hose coupling.

The embodiment illustrated in FIG. 4 is shown solely with the intention of showing that the end-art of the hose can be configured differently in accordance with the invention to achieve desired distribution of the outflowing air. For instance, the outer pipers 11 and 13 may have a length which is greater than the length indicated in FIG. 4. The pipes may also be provided with longitudinal rows of openings and closed at their respective ends.

It is also conceivable to introduce the air into said space from the head-end of the operating table instead of from the foot of the table, as in the illustrated case. At such an application the end part of the inlet hose may be formed in accordance with the example shown in FIG. 4, but without the central pipe 12.

In the described embodiments, the unit 9 is positioned at the head-end of the operating table, so as to enable the unit to be monitored and controlled by the anaesthetist, this position of the unit being normal in the case of surgical operations. It will be understood, however, that the unit 9 may alteratively be placed at the foot of the table 2 or beneath the table.

FIG. 4 illustrates schematically a temperature sensor 14 for measuring the temperature of the patient. This temperature sensor may be a sensor marketed by Hemex Medical, Stockholm, Sweden, under the trade name RSP Tympanic. The value indicated by the sensor 14 is registered and shown in a control panel (not shown) placed in the unsterile area, behind the anaesthetist's arch at the head-end of the operating table. The control panel is normally monitored by an anesthetist. In practice, several temperature sensors are placed at different positions of the patient's body and the warm-air unit is controlled in dependence on these temperature values, either directly by the anesthetist or some other person, or automatically by means of a suitable temperature control circuit. Such temperature control circuits are well known to the person skilled in this art and need not therefore be described in detail in this application. The warm-air unit is either controlled to vary the volume of warm air it delivers per unit of time or to vary the temerpature of the air delivered, or to achieve a combination of these variables. The embodiment illustrated in FIGS. 1–3 is also preferably provided with such temperature control means.

As will be understood, the described embodiments may also be used to deliver cold air instead of warm air, by replacing the warm-air unit with a cold-air unit. In this latter case, however, the rate at which the cold air is delivered will preferably be greater, so as to ensure that the cold air will flow around the patient.

It will be understood that the describe embodiments can be modified within the scope of the invention. For instance, the spacer sheet 8 can be omitted, particularly when the surgical drape is of the kind described in WO 94/01151 and promotes effective circulation of air between the drape and the patient's skin. It is also conceivable to provide a hose through that part of the drape 3 which hands down from the foot-end or the head-end of the operating table 2. This drape part may be provided with an opening for the hose. The last-mentioned openings may include a penetratable or resealable membrane. The surgical drape or the operating table may be provided with fastener devices which enable the hose to be detachable fastened to the drape or to the table. The hose may also be caused to discharge into the space beneath the operating table, although the operating table will preferably be provided with through-penetrating holes that allow air to pass therethrough in this latter case. The drape need not be totally impervious to air, although this is preferred, but may have a degree of air permeability of such smallness as to ensure that all air will leave the space beneath the operating table through the air outlet opening provided to this end. Thus, the expression "air-impervious surgical drape" as used in the descriptive part of this specification and in the Claims also includes surgical drapes that are not completely air-impervious but which fulfil the aforementioned criteria. The invention is therefor restricted solely by the contents of the following Claims.

What is claimed is:

1. A method for controlling the body temperature of a patient lying on an operating table during the course of a surgery in an operating theater, which comprises:
   placing over the patient at least one air-impervious surgical drape having an operation opening, such that the surgical drape hangs down from the operating table along its long sides and short sides, and forms a space which is closed at its top and sides, and has a roof and walls;
   providing an air-conditioning unit, and delivering conditioned air to the closed space; and
   providing an air outlet opening to enable air to flow out from the closed space.

2. The method according to claim 1, wherein the air outlet opening comprises a gap between the bottom edges of the surgical drape and the floor of the operating theater.

3. The method according to claim 1, further comprising, prior to placing said at least one surgical drape on the patient, placing a spacing sheet having an operation opening corresponding to the operation opening in the surgical drape, onto the patient; said spacing sheet being stiffer than the draped material.

4. The method according to claim 1, further comprising sensing the patient's temperature, and regulating at least one of the supply of conditioned air and the temperature of conditioned air as a function of the patient's temperature.

5. The method according to claim 1, wherein the conditioned air is delivered to a part of the closed space which lies above the top of the operating table.

6. The method according to claim 5, wherein the conditioned air is delivered trough an inlet hose which opens into an upper part of the closed space formed by the surgical drape.

7. The method according to claim 1, wherein a plurality of air-impervious surgical drapes, each having an aligned operation opening, are placed over the patient.

8. The method according to claim 7, further comprising placing a spacing sheet having an operation opening corresponding to the operation openings of the plurality of surgical drapes, onto said patient prior to placing the plurality of surgical drapes.

9. Apparatus for controlling the body temperature of a patient lying on an operating table during the course of surgery, the apparatus comprising:
   at least one air-impervious surgical drape having an operation opening, and structured and arranged to be placed over the patient such that the surgical drape hangs down from the operating table along its long sides and short sides, and forms an upwardly and laterally closed space having a roof and walls defined by said at least one surgical drape;
   a unit for delivering conditioned air to the closed space between the operating table and the surgical drapes; and
   an air outlet opening adapted to enable air to flow out from said closed space.

10. The apparatus according to claim 9, further comprising a spacing sheet adapted to be placed between the patient and the surgical drape; said spacing sheet having an operation opening corresponding to the operation opening of the surgical drape, and being stiffer than the drape material.

11. The apparatus according to claim 9, further comprising means for sensing the patient's temperature, and means for controlling the air delivery unit as a function of the patient's temperature.

12. The apparatus according to claim 11, further comprising means for controlling at least one of the volume of air delivered, and a temperature of air delivered, as a function of the patient's temperature.

13. The apparatus according to claim 9, wherein said at least one surgical drape comprises a plurality of air-impervious surgical drapes, each having an aligned operation opening.

14. The apparatus according to claim 13, further comprising a spacing sheet adapted to be positioned between the patient and the plurality of air-impervious surgical drapes; said spacing sheet having an opening aligned with the openings of the plurality of surgical drapes, and being stiffer than the drape material.

* * * * *